(12) United States Patent
Felder et al.

(10) Patent No.: US 10,617,457 B2
(45) Date of Patent: Apr. 14, 2020

(54) FORCEPS FOR HANDLING/HOLDING A MOBILE WEDGE PLATE

(71) Applicant: Stryker European Holdings I, LLC, Kalamazoo, MI (US)

(72) Inventors: Martin Felder, Niederbipp (CH); Marcel Abt, Solothurn (CH); Oliver Ammann, Bern (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 421 days.

(21) Appl. No.: 15/447,757

(22) Filed: Mar. 2, 2017

(65) Prior Publication Data
US 2017/0252081 A1 Sep. 7, 2017

Related U.S. Application Data

(60) Provisional application No. 62/303,063, filed on Mar. 3, 2016.

(51) Int. Cl.
*A61B 17/80* (2006.01)
*A61B 50/33* (2016.01)
(Continued)

(52) U.S. Cl.
CPC ........ *A61B 17/8095* (2013.01); *A61B 17/808* (2013.01); *A61B 17/8047* (2013.01);
(Continued)

(58) Field of Classification Search
CPC ... A61B 17/80; A61B 17/808; A61B 17/8095; A61B 50/33
(Continued)

(56) References Cited

U.S. PATENT DOCUMENTS

| 6,086,593 A | 7/2000 | Bonutti |
| 6,287,307 B1 | 9/2001 | Abboudi |

(Continued)

FOREIGN PATENT DOCUMENTS

| FR | 2785519 A1 * | 5/2000 | ........... A61B 17/151 |
| FR | 2785519 A1 | 5/2000 | |
| WO | 2017164861 A1 | 9/2017 | |

OTHER PUBLICATIONS

Spahn et al., "Biomechanical investigation of different internal fixations in medial opening-wedge high tibial osteotomy", Clinical Biomechanics, vol. 21, Issue 3, Mar. 2006, pp. 272-278.
(Continued)

*Primary Examiner* — Si Ming Ku
(74) *Attorney, Agent, or Firm* — Lerner, David, Littenberg, Krumholz & Mentlik, LLP

(57) ABSTRACT

The present invention includes devices, systems and methods for the storage, retrieval and placement of plates having wedges. A wedge plate tray includes an upper portion and at least one recessed portion, the recessed portion including a cavity sized to house the wedge and an additional cavity sized to accommodate placement and movement of an arm of an insertion instrument. The insertion instrument includes two arms connected at a hinge, a tip of each arm including a mating connector sized to engage a complementary mating connector on the wedge. In one embodiment of the method, the insertion instrument can be used to place the wedge plate in an osteotomy and where the wedge is a mobile wedge, a plate component can be adjusted to a desired position for securement while using the insertion instrument to hold the wedge in place in the osteotomy.

6 Claims, 5 Drawing Sheets

(51) Int. Cl.
*A61B 90/94* (2016.01)
*A61B 50/30* (2016.01)

(52) U.S. Cl.
CPC .............. *A61B 50/33* (2016.02); *A61B 90/94* (2016.02); *A61B 2050/3008* (2016.02)

(58) Field of Classification Search
USPC ................................................. 606/71, 86 B
See application file for complete search history.

(56) References Cited

U.S. PATENT DOCUMENTS

| | | | |
|---|---|---|---|
| 6,837,905 B1 | 1/2005 | Lieberman | |
| 7,326,218 B2 | 2/2008 | Sterett et al. | |
| 7,803,157 B2 | 9/2010 | Michelson | |
| 8,273,111 B2 | 9/2012 | Amato et al. | |
| 8,323,283 B2 | 12/2012 | Michelson | |
| 8,414,616 B2 | 4/2013 | Berrevoets et al. | |
| 8,690,944 B2 | 4/2014 | Bonutti | |
| 8,801,760 B2 | 8/2014 | Amato et al. | |
| 8,926,616 B2 | 1/2015 | Zalenski et al. | |
| 8,936,615 B2 | 1/2015 | Pappalardo et al. | |
| 8,998,903 B2 | 4/2015 | Price et al. | |
| 9,050,152 B2 | 6/2015 | Bonutti | |
| 9,072,555 B2 | 7/2015 | Michel | |
| 2009/0177203 A1 | 7/2009 | Reiley | |
| 2010/0004691 A1 | 1/2010 | Amato et al. | |
| 2011/0106084 A1* | 5/2011 | Gamache | A61B 17/7071 606/70 |
| 2011/0106169 A1* | 5/2011 | Zalenski | A61B 17/7071 606/279 |
| 2016/0000486 A1 | 1/2016 | Leduc et al. | |

OTHER PUBLICATIONS

Anchorage Plating System, Operative Technique, Foot & Ankle, Content ID: AN-ST-1 Rev. 2, Aug. 2015, Literature Number: 982380, Manufactured by Stryker GmbH, Copyright Stryker, Aug. 2015.

* cited by examiner

FORCEPS FOR HANDLING/HOLDING A MOBILE WEDGE PLATE

CROSS-REFERENCE TO RELATED APPLICATIONS

This application claims the benefit of the filing date of U.S. Provisional Patent Application No. 62/303,063, filed Mar. 3, 2016, the disclosure of which is hereby incorporated by reference herein.

BACKGROUND OF THE INVENTION

The present invention relates to improved devices, systems and methods for storing and retrieving implants and performing osteotomy procedures.

An osteotomy is a surgical procedure whereby a bone is cut to shorten, lengthen or otherwise change its alignment. It may be performed to correct deformities such as a hallux valgus, a progressive forefoot deformation, or to relieve pain from arthritis, especially in the hip or knee. The procedure usually entails either: the removal of a typically wedge-shaped portion of a bone by cutting transverse to the long axis of the bone, whereupon the bone can be "closed," i.e., fused together at the space and allowed to heal; or a simple partial cut transverse to the long axis, whereupon the bone can be "opened" and fixated with an appropriate device. For example, an implant may be inserted into the space, and/or a bone plate may be affixed to the bone adjacent to the space, to maintain or increase the space. The "closing" or "opening" changes the spatial relationship between the remaining portions of the bone in order to adjust its alignment or length.

Open-wedge osteotomy refers to a specific type of osteotomy procedure in which a partial cut transverse to the long axis of the bone is made and subsequently opened. The correction is maintained by using an appropriate fixation device, such as, for example, a bone plate with screws. Additionally, a wedge can be included with the bone plate to fill the space that is opened so that the bone can return to a load-bearing state and also to facilitate bone healing. The implanted wedge helps to maintain the opened space by allowing the bone to transmit load to the wedge, thereby preserving the surgeon's aimed reduction or expansion of the angle of the bone before final locking of the plate with bone screws. The wedge also keeps the osteotomy open to allow insertion of locking or non-locking bone screws into the bone to fix the bone plate to the bone.

These procedures have typically been performed using static wedge plates, such as that shown in FIGS. 1A-1D. The static wedge plates shown include a bone plate 2 and a wedge 4 integrally formed on a bottom surface of the plate. The bone plates also include a plurality of holes for the placement of screws. The holes on the bone plate are positioned so that the plate is securable on both sides of an osteotomy 5 as is shown in FIG. 1E, where the static wedge plate is implanted in a foot bone. Proximal to each end, the bone plate 2 further includes a hole adapted for placement of K-wire. U.S. application Ser. No. 14/793,215 ("the '215 application"), the disclosure of which is hereby incorporated by reference herein in its entirety, discloses similar plates wherein a wedge is formed separately from the plate and thereafter assembled thereto. This design allows for the situation of the wedge at varying positions with respect to the plate.

Placement of existing static wedge plates involves orienting the plate such that the integrally formed wedge extends into the resultant space of the bone created by making one or more transverse cuts. This placement may utilize any number of tools or can simply be performed by hand by the surgeon. Placement of a mobile wedge plate like that disclosed in the '215 application is somewhat more difficult. Not only is it necessary to guide the wedge into the resultant space, but it is also necessary to maintain the wedge in position with respect to the plate.

Thus, a need exists to improve the instruments, devices, systems and methods used to perform osteotomy procedures to reduce errors in placement of implants, to reduce the need for additional intraoperative procedures, and to improve storage and retrieval of implants.

BRIEF SUMMARY OF THE INVENTION

The present invention generally relates to systems and methods for the storage and placement of bone plates used in osteotomies. A first aspect of the invention is an implant system that includes a bone plate, a wedge and an insertion instrument. The bone plate is configured to be secured to a bone. The wedge is coupled to the bone plate and includes one of a cavity or a projection. The insertion instrument includes an element complementary to the wedge so that if the wedge has a cavity, then the insertion instrument has a projection, and vice versa. The features of the wedge and the insertion instrument are configured so that the insertion instrument engages with the wedge.

In another embodiment, the wedge is moveable with respect to the bone plate. In yet another embodiment, the insertion instrument includes first and second arms pivotally connected to each other. The first arm includes one of a first cavity or a first projection. This cavity or projection engages with the other of the first cavity or first projection located on the wedge. Similarly, the second arm includes one of a second cavity or a second projection. This cavity or projection engages with the other of the second cavity or second projection located on the wedge. In yet another embodiment, the insertion instrument can engage the wedge in a first configuration such that the bone plate is moveable with respect to the insertion instrument and in a second configuration such that the bone plate is fixed with respect to the insertion instrument.

In other embodiments, the wedge includes first and second cavities or first and second projections. The first cavity or projection is formed on a first surface of the wedge and the second cavity or projection is formed on a second surface of the wedge opposite the first surface. In other embodiments, the system also includes a tray. The tray is adapted to hold the bone plate where the bone plate is coupled to the wedge. In yet another embodiment, the tray includes an instrument cavity. The instrument cavity is adapted to receive a portion of the insertion instrument. It is also adapted to allow the insertion instrument to engage the wedge. In a variant, the tray further comprises a recessed portion to hold the bone plate. The recessed portion includes at least a first recessed surface and a second recessed surface. The second recess is recessed relative to the first and is adapted to hold the wedge in place when the wedge is stored in the tray.

Another aspect of the invention is a tray for the storage of wedge plates. The tray includes a body with first and second recessed portions, as well as a cavity. The first recessed portion has a perimeter sized to accommodate a bone plate. The second recessed portion is recessed relative to the first recessed portion and includes a perimeter sized to accommodate a wedge. The cavity is adjacent to and in communication with the second recessed portion. The cavity is sized so that an insertion instrument can be disposed within the cavity and can be manipulated while disposed.

In another embodiment, the tray also includes a second cavity so that there is a first and second cavity in the tray. The cavities are located so that each extend from different sides of the second recessed portion. In a variant, a bottom surface of the first and second cavities are at a depth different than a depth of the first recessed portion. In a further variant, each cavity includes a length measured from an edge of the first recessed portion to a tip and is defined by two parallel walls between the edge of the first recessed portion and the tip. In yet another variant, the length and depth of each cavity are sufficient for an adjustment of an arm of the insertion instrument along the length and depth of the cavity.

In yet another aspect of the invention, a first embodiment provides a surgical method that entails engaging an insertion instrument with a wedge movably connected to a bone plate; orienting the wedge with respect to the bone plate; and manipulating the insertion instrument to place the wedge between first and second bone portions and the plate against the two bone portions.

In another embodiment, the wedge and bone plate are held in a tray. With the elements in this position, the engaging step further includes placing a portion of the insertion instrument in a first position into first and second cavities in the tray. This is followed by moving the insertion instrument to a second position where the wedge is captured by the insertion instrument. In a variant, the engaging step further involves a first mating connector of the insertion instrument engaging a complementary second mating connector of the wedge and a third mating connector of the insertion instrument engaging with a complementary fourth mating connector of the wedge.

In another embodiment, the engaging step includes engaging both the wedge and the bone plate with the insertion instrument. That is, both the wedge and the bone plate are engaged at the same time. In other embodiments, the orienting step occurs prior to the engaging step. In still further embodiments, an additional resecting step is taken where a bone is resected to create the first and second bone portions. In other embodiments, additional steps are taken including placing a first screw through the bone plate and into the first bone portion and placing a second screw through the bone plate and into the second bone portion.

DETAILED DESCRIPTION

Although the embodiments described below and shown in the figures are directed to specific implants and procedures, it is to be understood that the concepts and novelty underlying the present invention could be utilized for other types of procedures, including other osteotomy procedures such as Cotton osteotomies, Evans osteotomies, high tibial osteotomies, and other open wedge osteotomies. Moreover, although described in connection with the correction of hallux valgus in the foot, the present invention has application in other areas of the human body, including the ankle, knee, hip, spine, and even maxillofacial areas, such as the jaw or chin. Likewise, the particular structures depicted are merely exemplary, and may vary widely while still employing the inventive features of the present invention.

Figures 1A, 1B, 1C, 1D:
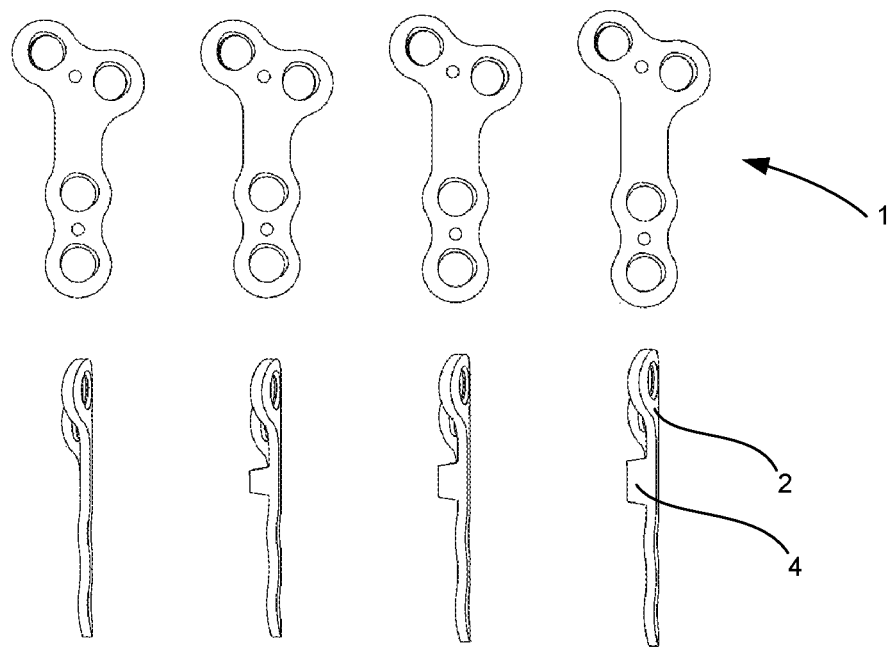
FIGS. 1A-D illustrate several prior art static wedge plates.
Figure 1E:
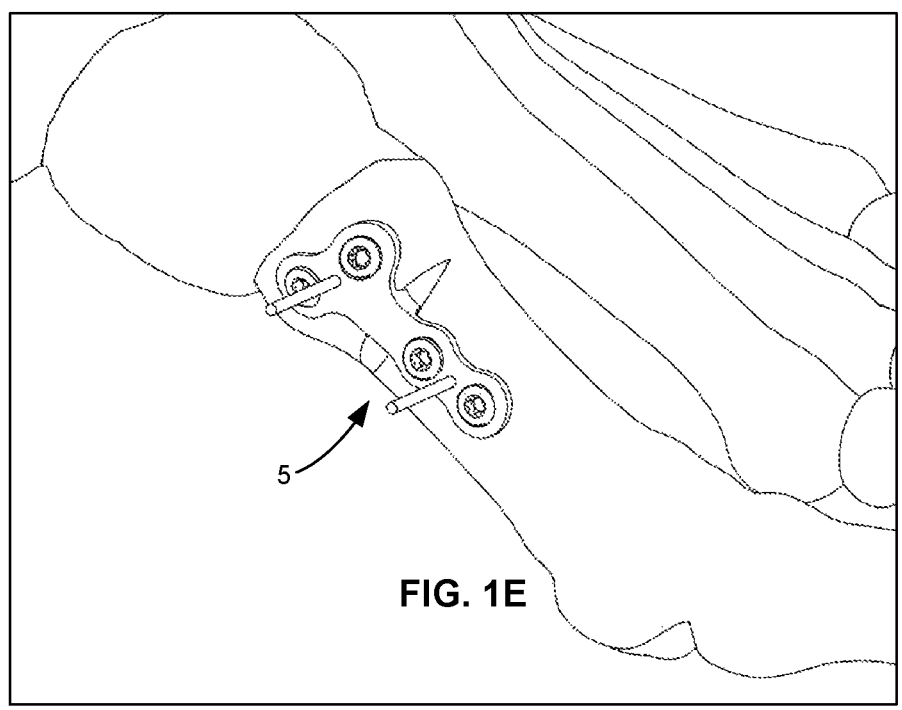
FIG. 1E illustrates one of the static wedge plates of FIGS. 1A-D implanted in a foot bone.
Figure 2:
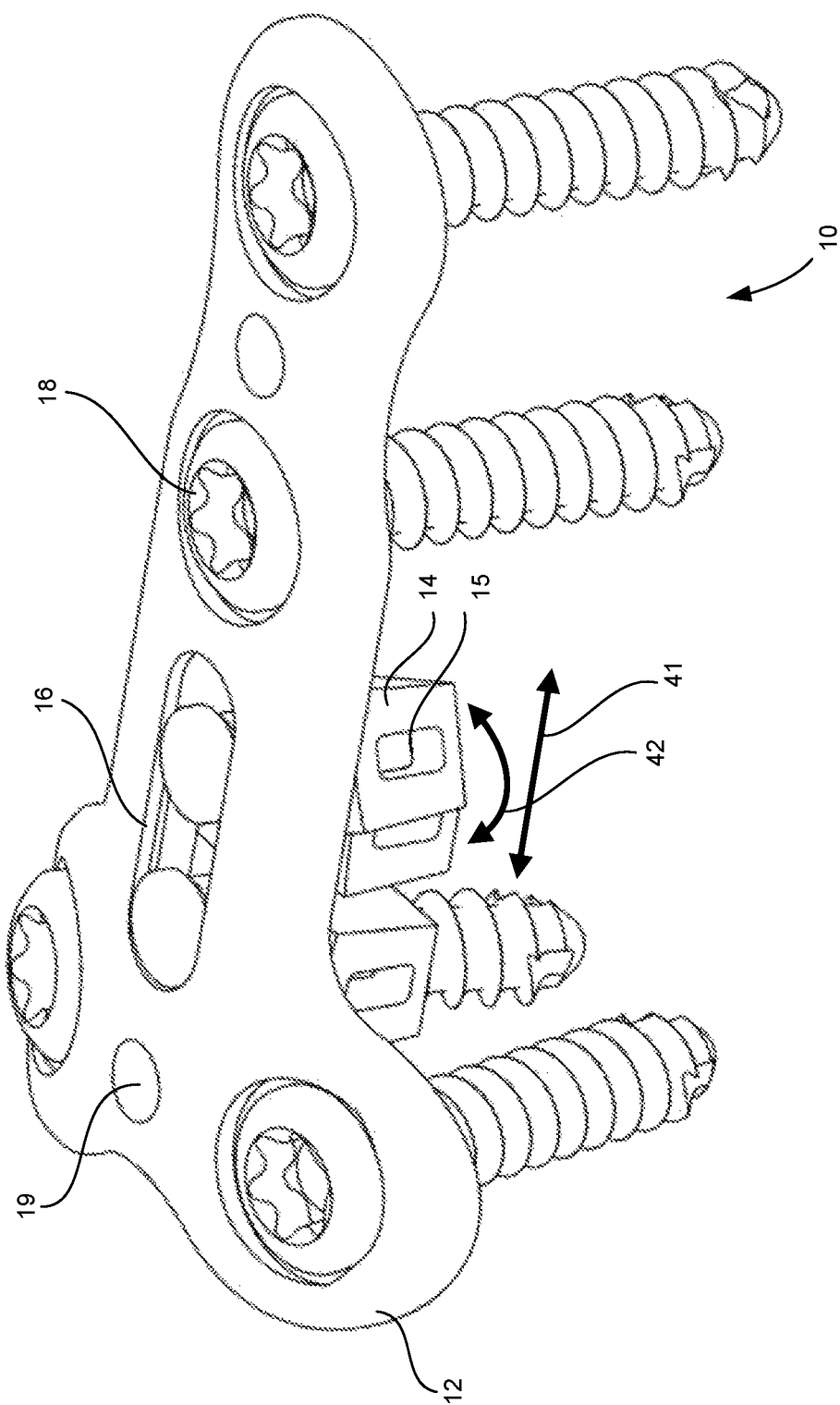
FIG. 2 illustrates a perspective view of a mobile wedge plate according to one embodiment of the present invention.

The various aspects of the invention described below are suitable for use with a wide variety of wedge and bone plate combinations where the wedge is coupled to the bone plate. One exemplary combination includes a wedge coupled to a bone plate where the wedge is longitudinally translatable and rotatable relative to the bone plate (hereinafter, "mobile wedge plate"), but could still have applicability to plates with integrally formed wedges. FIG. 2 illustrates one embodiment of the mobile wedge plate 10 that is adapted for use with the wedge holding forceps and wedge plate tray described herein. The mobile wedge plate 10 includes a bone plate 12 and a wedge 14.

As shown, bone plate 10 includes a track 16 positioned and sized to allow for translation 41 and rotation 42 of the wedge 14. The bone plate also includes holes 18 sized for the placement of screws through the plate and into surrounding bone. Bone plate 12 also includes at least one hole 19 adapted for the placement of K-wire. In other variants, the holes 18, 19 can be sized for the placement of a variety of screw or K-wire types, sizes and quantities, and can be situated in any configuration on the plate. Likewise, although plate 10 is shown for a particular use in the foot, it can exhibit any configuration necessary for use elsewhere in the body.

The wedge 14 includes an engagement portion having a stem and a head, like that more fully disclosed in the '215 application. The wedge is positioned at an approximately orthogonal position relative to a length of the bone plate 12 and is coupled to the bone plate 12 through the engagement portion wherein the stem extends through the track 16 and a lip of the head keeps the stem and the wedge from separating from the bone plate. The wedge 14 is longitudinally translatable along the length of the track 16. As the stem has a generally round cross section, the wedge 14 is also rotatable at any location on the track 16. In a variant, the wedge can further be adapted to include a locking element that can be used to lock the wedge at a particular angle or position relative to the bone plate.

Outer surfaces of the wedge 14 are generally planar. On the two opposite facing surfaces perpendicular to the length of the bone plate, the wedge includes wedge mating connectors 15. In the embodiment shown in FIG. 2, the wedge mating connectors are remote from corners of the wedge 14. In a variant, only the lateral sides of the wedge mating connectors are remote from edges of the wedge 14. In another variant, the wedge mating connectors are remote from the lateral sides and bottom edges of the wedge 14, but not the top edges proximal to the bone plate 12. In still further variants, the wedge mating connector on one side of the wedge is a different size than the wedge mating connector on the other side of the wedge. In yet another variant, the wedge mating connector on one side of the wedge is a different shape than the wedge mating connector on the other side. One example of such wedge mating connectors 15 are wedge cavities as shown in FIG. 2. In another example, the wedge mating connectors are projections. Mating connectors in the form of projections include pins, elevated portions, bosses or other shapes configured to be engagable with a complementary cavity in an instrument. Complementary mating connectors included on a tool or instrument are described in detail below.

Figure 3:
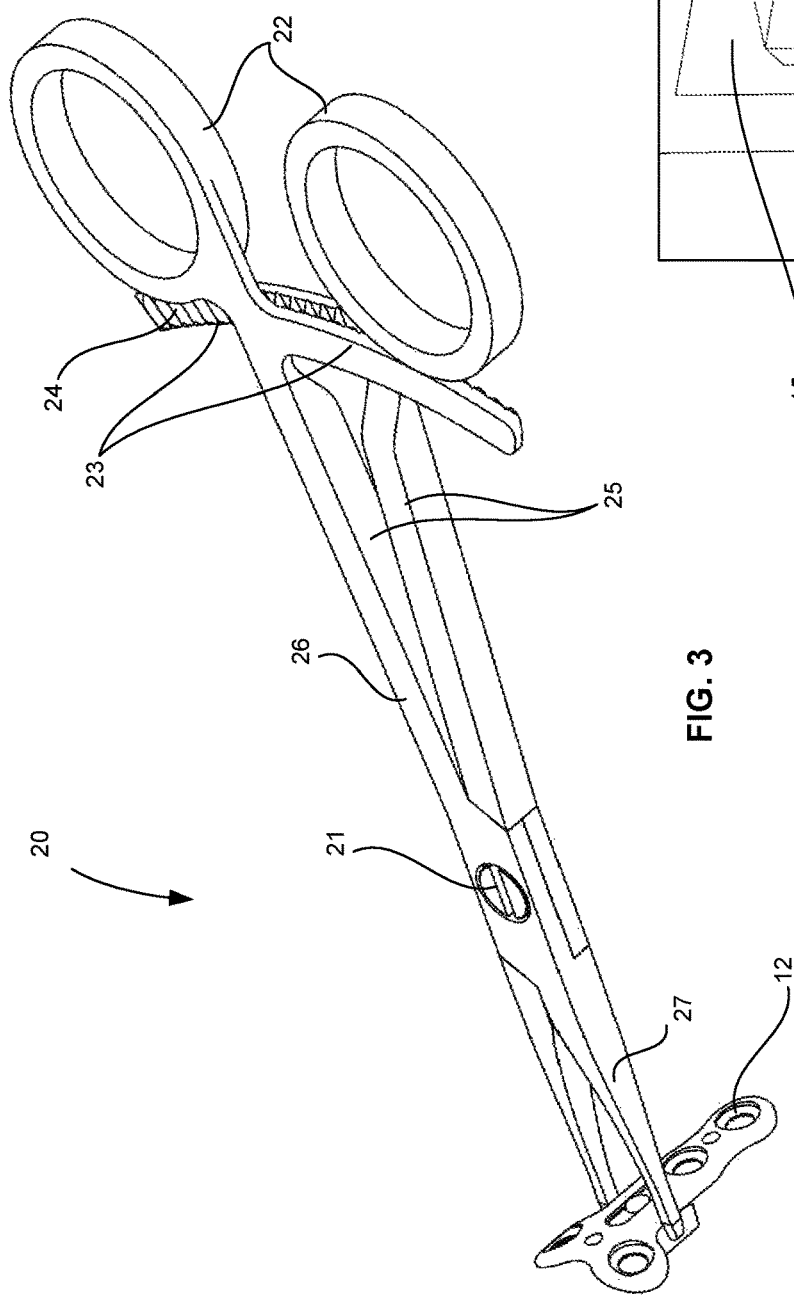
FIG. 3 illustrates a perspective view of a wedge holding forceps of the present invention engaged with the mobile wedge plate of FIG. 2.

An insertion instrument in the form of wedge holding forceps 20 is shown in FIG. 3. Forceps are a typical instrument for use in picking up and placing implants, such as plates, into and through surgical openings, for instance, in the placement of wedge plates during osteotomy procedures. The wedge holding forceps 20 include two components connected at a hinge 21 that functions as a pivot point. The hinge as shown in FIG. 3 is a Pin-type hinge. In a variant, the hinge can be any type known to those of skill in the art. Each component has unitary shading as shown in FIG. 3 and includes a ring handle 22, a ratchet 23 and an arm 25.

The ring handle 22 of each component is generally circular and allows a user's finger(s) to pass through for grip. The ring handle is connected to the arm 25 at one location, with the arm 25 extending from the ring handle on a generally linear path. The ratchet 23 extends from the arm 25 of each component at a location proximal to the ring handle 22. The ratchet has a length so that in many of the wedge holding forceps positions, it overlaps with a longitudinal axis of the arm of the opposing forceps component. The length of the ratchet 23 is arcuate so that in a direction toward the opposing component of the forceps, it curves away from the ring handle on the opposing component. One surface of each ratchet 23 includes serrations 24 adapted to interconnect with serrations on the opposing component. In FIG. 3, the serrations 24 on the ratchet of one component face upward as shown and the serrations 24 on the other component face downward so that the respective serrations face each other. This provides interconnectivity between the components of the forceps in open and closed positions and positions in between.

The arm 25 of each component includes an upper portion 26 and a lower portion 27. The upper and lower portions are divided by the hinge 21. The upper portion 26 is generally linear and has a length extending from the ring handle 22 to the hinge 21. The lower portion 27 is generally linear through approximately the same axis as the upper portion and has a length extending from the hinge 21 to a tip. Although the lower portion 27 of the arm is generally linear, the tip of the arm includes an instrument mating connector 28, complementary to the wedge mating connector 15. One example of such an instrument mating connector is a projection 28, best shown in FIG. 4, having the appearance of a tooth. The projection 28 has a length extending inward from the lower portion 27 toward the opposing component of the wedge holding forceps at an angle to the length of the lower portion. A cross sectional shape of the projection 28 of the arm is rectangular and is sized to engage the complementary wedge mating connector 15 of the wedge 14 forming part of the mobile wedge plate 10, in this case, a wedge cavity. The projection 28 includes an end face 29 that is perpendicular to a length of the projection so that a longitudinal axis of the length of the projection passes through the end face 29. In another variant of the projection example, a projection that engages with the wedge cavity is an extension of projection 28 and has a smaller cross section than projection 28.

In another example, the projection can be sized so that a cavity or recess exists within the end face of the projection. The cavity can be sized to engage with the corresponding mating connector of the wedge plate, in this case, a projection, so that the cavity of the instrument receives the projection of the wedge in a secure manner. The cavity can be any shape provided it complements the shape of the projection. In a variant of this example, the cavity can be directly on the surface of the lower portion 27 of the arm itself so that the insertion instrument includes no projections. In such a variant, the projections of the wedge are long enough to ensure engagement between the projections of the wedge and the cavity of the instrument where closure of the arms of the instrument is limited by a width of the bone plate. Of course, in other embodiments, the mating connector of the insertion instrument can be of any shape suitable for engaging the mating connector of the wedge plate. It is also contemplated to provide wedge 14 with one cavity and one projection and forceps 20 with one projection complementary to the cavity of the wedge and one cavity complimentary to the projection of the wedge. Additionally, more than one of either the cavity or projection may be provided in each component.

Figure 4:
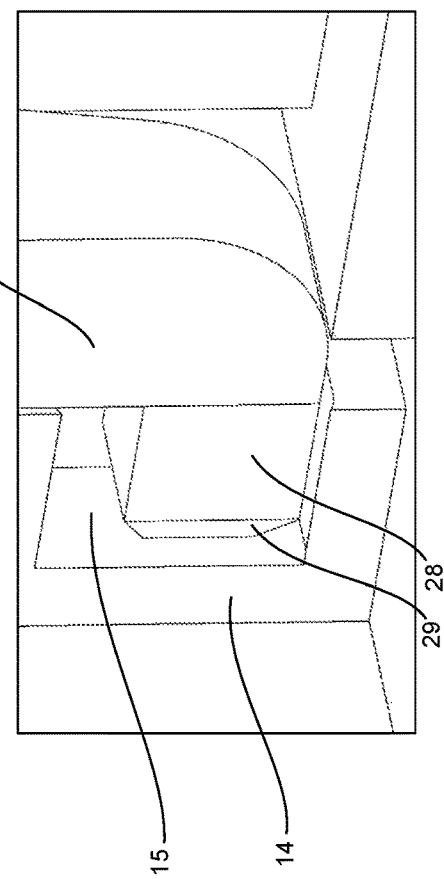
FIG. 4 is a close up view of an engagement between the forceps and mobile wedge plate of FIG. 2.

As shown in FIG. 4, the longitudinal axis of the instrument mating connector 28 is at an acute angle relative to a longitudinal axis of the length of the lower portion 27 of the arm. In a variant, the angle between the longitudinal axis of the instrument mating connector 28 and the longitudinal axis of the lower portion 27 can be ninety degrees. In another variant, it can be greater than ninety degrees. In still further variants, a plane through the end face 29 of the instrument mating connector 28 can be at an acute angle relative to the longitudinal axis of the projection. In other variants, the plane through the end face 29 can be at an obtuse angle relative to the length of the instrument mating connector 28. The instrument mating connector 28 on the arm of one component of the wedge holding forceps is the same size and shape as the instrument mating connector 28 on the arm of the opposite component. In a variant, however, the instrument mating connector on one arm can be a different size than the instrument mating connector on the other arm. In yet another variant, the instrument mating connector on one arm can be a different shape than the instrument mating connector on the other arm.

In addition, it is to be understood that the arm 25 of each component shown in FIG. 3 is monolithic between the handle 22 and the instrument mating connector 28. In this way, the hinge 21 that connects each arm 25 ensures that movement of the instrument mating connector 28 on each arm is directly correlated to the movement of each handle 22. In other words, the connection of the arm 25 of each component to the hinge 21 allows each arm to pivot about the hinge 21. Of course, in variants, the arm of each component can include two or more sub-components to complete the arm structure and can be connected together using any means known to those of ordinary skill in the art. It is also contemplated to form forceps such that they open and close in different fashions. For instance, forceps according to the present invention could include a three bar linkage that would allow them to open and close with the arms remaining in a parallel orientation.

In any one of the above embodiments, the cross sectional shape of the arms, ratchet and/or handles can be square, rounded, elliptical or any other shape known to those of ordinary skill in the art. The ratchet of one component can be any structure, either monolithic with the arm of each component or separate, that functions to interconnect with the ratchet of the other component. The handles can be oval in shape or any other handle shape or type known to those of ordinary skill in the art. In other embodiments, the insertion instrument can be any tool with two arms where each arm is adapted to include a mating connector at an engagement end and has a range of movement between an open and closed position so that movement is sufficient to engage a wedge plate and to fit within instrument cavities in the tray as described herein.

One advantage of the insertion instrument is that it allows a user to accurately adjust and hold the wedge relative to the bone plate of the mobile wedge plate prior to final positioning in the osteotomy. This can be prior to insertion of the wedge into the osteotomy or while the wedge is in the gap between bones in the osteotomy. In both circumstances, the insertion instrument holds the wedge in place while another means are used to rotate the bone plate relative to the wedge. This significantly reduces the need for intraoperative procedures to adjust the mobile wedge plate as it can be adapted to the particular osteotomy at issue prior to final placement. For example, whether the osteotomy is perpendicular to a length of the subject bone or whether it is at another angle, the angle between the bone plate and the wedge can be adjusted to match the actual conditions at the surgical site.

Another advantage of the insertion instrument is that it can be used to hold the wedge in place to rotate the bone plate to an extent sufficient for accurate alignment of the bone plate with the bone to be secured. With the bone plate in proper position for securement, the insertion instrument can continue to hold the wedge while the user performs preliminary plate fixation via drilling. In the same way, the wedge can be held while the user performs screw insertion to secure the bone plate to the bone. It is also envisioned that the insertion instrument can be configured such that upon engagement with the wedge, the bone plate is also engaged. This can result in a fixed construct upon application of the insertion instrument to the bone plate and wedge. A surgeon can align the wedge in the desired position with respect to the plate before application of such insertion instrument. This is advantageous in that it takes an otherwise unfixed set of components and fixes them for placement within the body.

Figure 5:
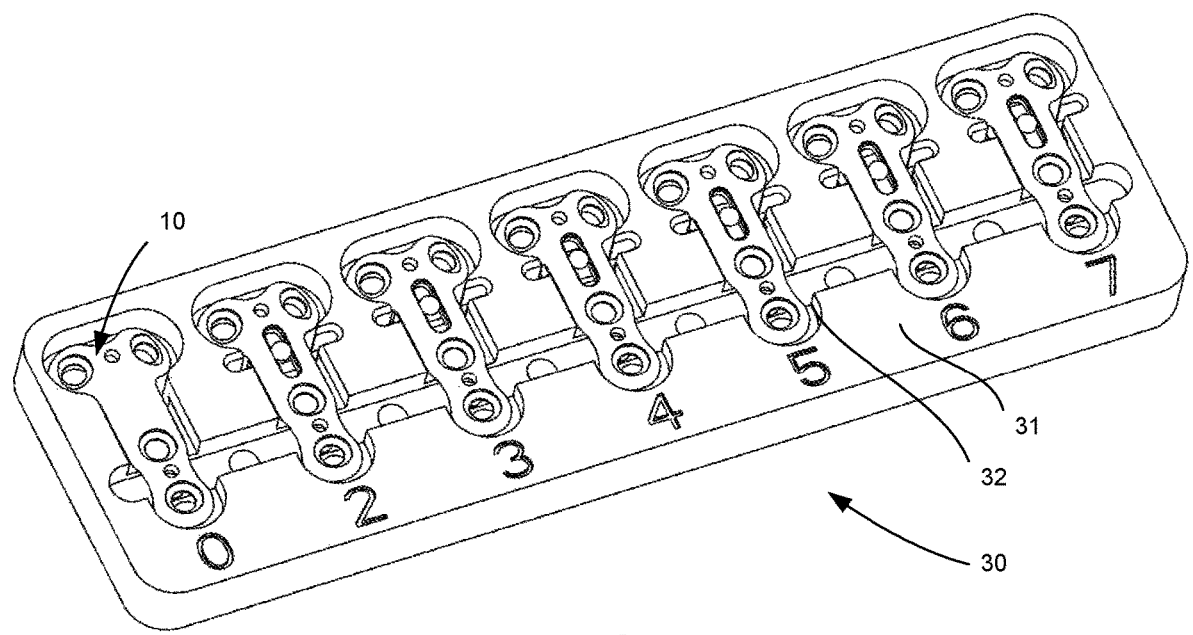
FIG. 5 illustrates a wedge plate tray according to one embodiment of the present invention having a plurality of mobile wedge plates disposed within recessed portions thereof.

In another aspect, the present invention relates to a wedge plate tray adapted to receive wedges coupled to bone plates and the insertion instrument. One embodiment of the wedge plate tray 30 is illustrated in FIG. 5. The wedge plate tray 30 is generally rectangular in shape and includes a maximum depth that is greater than the depth of wedges coupled to bone plates. A top surface includes a generally planar outer portion 31 and a plurality of recessed portions 32. In FIG. 5, each of the recesses adjacent to a numeric marking represents a recessed portion 32. For example, "0", "2", "3" and so on. Each recessed portion 32 extends over an area bounded by the outer portion 31 of the top surface so that no recessed portion 32 extends to a perimeter of the tray 30. The surface area of each recessed portion 32 is slightly larger than a surface area of a bone plate 12 and each recessed portion is oriented so that adjacent recessed portions are parallel to one another and a length of each recessed portion is perpendicular to a length of the tray 30. However, the recessed portions 32 are preferably sized to allow for a snug fit with the bone plate and wedge in order to hold them in position within the tray. Tray 30 can also include a cover in the form of a removable lid or even be configured similar to a blister pack with a peel off cover.

Figure 6:
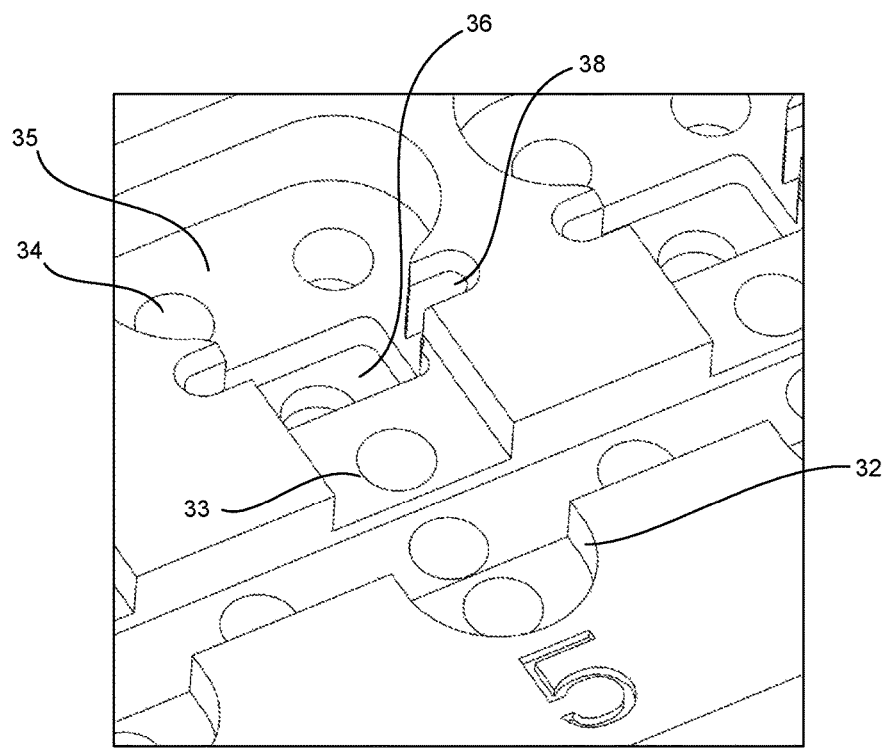
FIG. 6 illustrates a close up view of a recessed portion of the wedge plate tray of FIG. 5.

As best shown in FIG. 6, each recessed portion includes a step so that one side is recessed to a greater extent than the other. Thus, the recessed portion is divided into a deep recess 35 and a shallow recess 33, where the step separates each. The depth and shape of the recess at different locations on the recessed portion ensures that the mobile wedge plate 10 can be firmly secured into the tray 30. In other words, the plate is held securely in place by the shape of the recess in the tray. As shown in FIG. 5, the wedge plate tray 30 includes additional cavities 34 on the recessed surfaces. FIG. 6 illustrates that two of the cavities 34 are located in the shallow recess 33 of the recessed portion while the other two are in the deep recess 35. Each cavity is sized to permit water passage. Water passage can occur, for example, when cleaning the tray 30.

Figure 7:
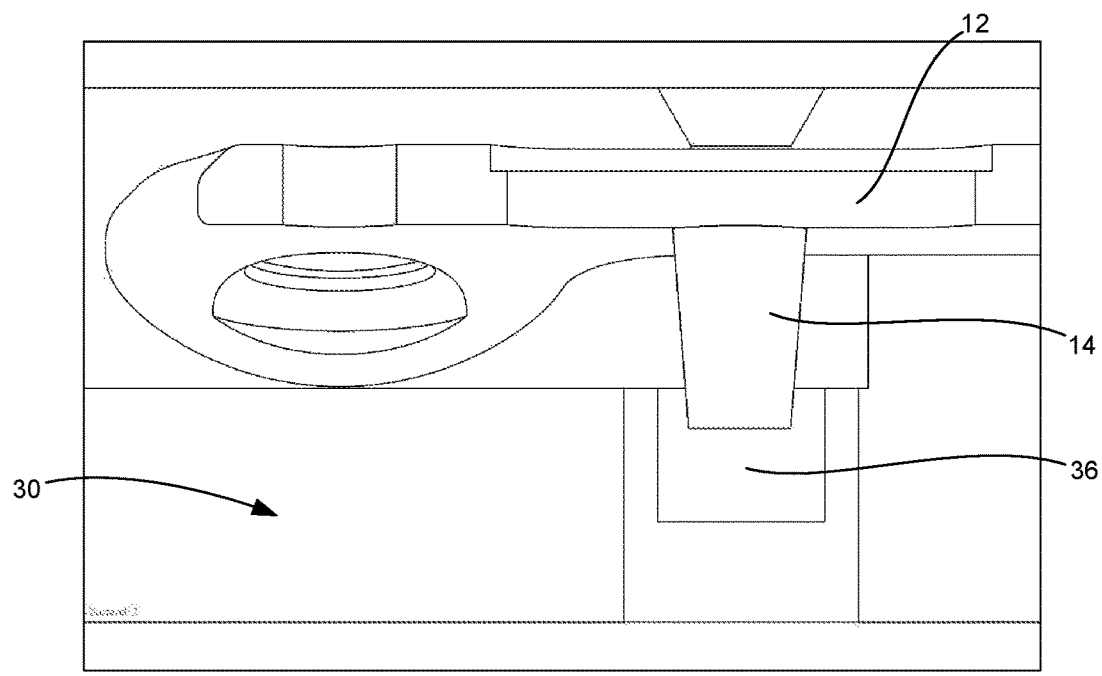
FIG. 7 illustrates a close up cross sectional view through a recessed portion of the wedge plate tray of FIG. 5 with a mobile wedge plate disposed therein.

Within a surface of the deep recess 35 is yet another recessed surface to accommodate placement of the wedge coupled to the bone plate when the bone plate is positioned in the wedge plate tray 30. As shown in FIGS. 6 and 7, a wedge recess 36 is generally rectangular in shape with beveled corners and is centered on a width of the recessed portion 32. Although generally speaking, as described above, the outer perimeter of the recessed portion 32 is the shape of a perimeter of the top surface of the bone plate 12, the recessed portion does extend outward from this perimeter at two locations. At each of these locations is a tray cavity for an instrument 38 having a length perpendicular to a longitudinal axis of the wedge recess 36. The length of the cavity extends from the perimeter of the recessed portion to a tip and is defined by parallel walls, visible in FIGS. 6 and 8. The instrument cavities 38 extend to a depth of the deep recess 35 and are open into the recessed portion 32 so that access between the instrument cavities 38 and the deep recess 35 is unimpeded throughout the depth of the recess. In other words, the instrument cavities 38 are in communication with the deep recess 35. Each cavity 38 is located on an opposite side of the perimeter of the recessed portion 32. The instrument cavities 38 are sized to accommodate the insertion of each arm of the wedge holding forceps 20 from both sides of the mobile wedge plate 10. The size of the instrument cavities 38 is sufficient not only to allow insertion of each arm, but further to allow manipulation of the handles 22 so that the mobile wedge plate 10 can be retrieved or released while the forceps 20 are inside the cavities 38. Other embodiments with different cavity 38 geometry are discussed in detail below.

In other embodiments, the instrument cavities 38 can be recessed to a lesser or greater extent than the deep recess 32. In a variant, the depth of the instrument cavity on one side of the recessed portion can be different than the depth on the other side. In any one of the above embodiments, the length of mobile wedge plates can be oriented so that a centerline through the length of each plate passes through a common axis, and/or the recessed portions can include additional cavities. Of course, other embodiments can include additional cavities or recessed portions extending outward from the outer perimeter of the recessed portion 32.

In another embodiment, the wedge plate tray includes an outer portion and a single recessed portion sized to accommodate a single mobile wedge plate. In other embodiments, the wedge recess 36 can be elongated to accommodate longitudinal movement of the wedge 14 along the track 16 of the bone plate 12 while the mobile wedge plate is secured in the tray 30. A width of the instrument cavities 38 can also be sized to accommodate rotation of the arms 25 of the wedge holding forceps 20 about the center of the recessed portion 32 of the tray. Through the combination of the enlarged wedge recess 36 and instrument cavities 38, the wedge of a mobile wedge plate secured in a tray may be longitudinally translated and/or rotated relative to the bone plate while secured in the tray 30 using the forceps 20.

In any one of the above embodiments, further to the recessed portions already described, the wedge plate tray can include additional recessed portions. Additional recessed portions can include one or more recessed levels and can further include additional cavities within the one or more recessed levels. In any one of the above embodiments, the plurality of recessed portions, each adapted for the storage of a wedge plate, can be of varying size with respect to each other. For example, one recessed portion can be sized for the placement of a mobile wedge plate including a bone plate five inches in length, while another recessed portion can be sized for the placement of a mobile wedge plate including a bone plate ten inches in length. As these examples illustrate, the embodiments contemplated herein can also include a wedge plate tray with recessed portions sized for the placement and storage of plates of a size other than that depicted in FIG. 5. In any one of the above embodiments, the wedge plate tray can be adapted for use with wedges coupled to bone plates that are not mobile wedge plates.

Advantages of the wedge plate tray include that it allows for the secure storage of bone plates with wedges secured to the bottom thereof. Another advantage of the wedge plate tray is the unique combination of a recessed portion for the placement of the bone plate into the tray, an additional recessed surface in the recessed portion for the insertion of the wedge coupled to the bone plate, and additional cavities located adjacent to the recessed portion so that an insertion instrument can be inserted to retrieve the bone plate.

Figure 8:
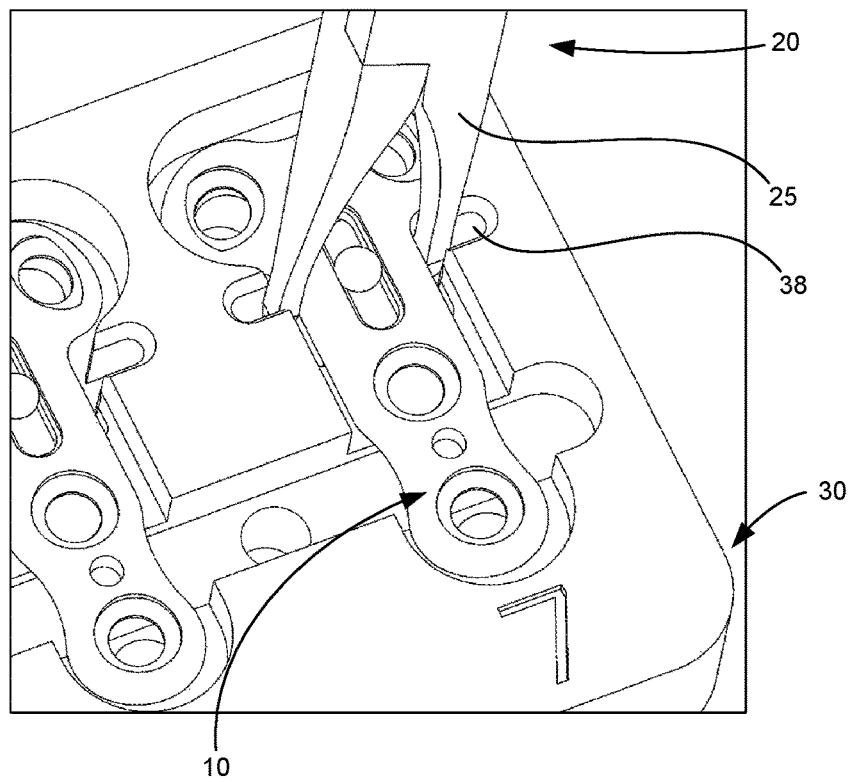
FIG. 8 illustrates the forceps of FIG. 3 engaging a mobile wedge plate disposed within a recessed portion of the wedge plate tray of FIG. 5.

In yet another aspect, the present invention relates to a method of using the wedge holding insertion instrument in connection with the wedge plate tray to retrieve and place a wedge coupled to a bone plate for surgical procedures. In one embodiment, one or more mobile wedge plates 10 are stored in the recessed portions 32 of the wedge plate tray 30, as shown in FIG. 5. The mobile wedge plates 10 are positioned in the tray so that the wedge of each mobile wedge plate fits into the wedge recess 36 of the recessed portion 32. To retrieve one of the mobile wedge plates 10 for placement at a surgical site, such as an osteotomy, the user utilizes wedge holding forceps 20 as shown in FIG. 3 and adjusts the arms 25 into an open position by spreading the ring handles 22 apart from one another until the lower portions 27 of the arms are slightly wider than the width of the mobile wedge plate 10. The user then lowers the forceps so that a portion of each arm 25 enters a forceps cavity 38 of the tray 30, as shown in FIG. 8. With a portion of the arms in place within the forceps cavities 38, the user brings the ring handles 22 closer together so that the instrument mating connector 28 of each arm 25 engages with one of the complementary wedge mating connectors 15 of the wedge 14, as shown in FIG. 4. With the arms engaged, load from the mobile wedge plate is borne by the mating connector of each arm as the user lifts the forceps to remove the mobile wedge plate 10 from the wedge plate tray 30. In a variant, the user can use the forceps 20 to move the wedge 14 along the track 16 of the plate 12 or rotate the wedge relative to the plate prior to lifting the forceps 20 from the tray 30. Alternatively, the wedge can be longitudinally translated or rotated relative to the plate prior to being engaged by the forceps. In another variant, the user can manipulate the arms once partially inserted into the forceps cavities 38 to assist in locating the wedge mating connectors 15 of the wedge for engagement. In yet another variant, forceps 20 may not only engage wedge 14, but also a portion of the bone plate in order to fix both components in position with respect to the forceps 20.

With the wedge holding forceps 20 engaged to the mobile wedge plate 10 and the mobile wedge plate removed from the tray 30, the forceps are then used to transport the mobile wedge plate 10 to a desired surgical site. The user then lowers the forceps 20 so that the arms of the forceps and the wedge 14 are positioned between bone on both sides of the osteotomy. In this position, the bone plate 12 traverses both sides of the osteotomy. Steps known to those of skill in the art are then used to secure the bone plate 12 of the mobile wedge plate 10 to the bone. For example, screws 18 are inserted into the bone through each hole 18 in the bone plate 12. In one variant, the osteotomy includes resection of a single bone to create first and second bone portions.

In another embodiment, the method of the above embodiment can further include the step of rotating and/or translating the wedge relative to the bone plate while the user continues to hold the wedge holding forceps to secure the wedge after the mobile wedge plate is removed from the tray. Rotating or translating of the wedge can be done prior to or even after placement of the mobile wedge plate into the osteotomy. This ensures proper alignment of the mobile wedge plate to the osteotomy and adjacent bone structure for both placement of the wedge and securement of the bone plate to the desired bone surfaces. In other embodiments, where forceps are designed to hold the plate and wedge in a fixed position, this alignment can be done after removal of the forceps.

In another embodiment, a method is contemplated where the wedge holding forceps can be used to retrieve the mobile wedge plate and transport it to the wedge plate tray. The user first retrieves the forceps and then adjusts the arms as described above to position the forceps for the retrieval of the mobile wedge plate. The forceps are then lowered and closed as necessary to engage with the mobile wedge plate. With the wedge engaged, the forceps are used to transport the mobile wedge plate to the wedge plate tray. As above, the user then lowers the forceps so that each arm enters the forceps cavity of the tray. With the arms in place within the forceps cavities, the user opens the ring handles moving them further apart, and thus disengaging the teeth of the arms from the wedge of the mobile wedge plate. The user lifts the forceps, leaving the mobile wedge plate stored in position within a recessed portion of the tray.

In yet another embodiment, static wedge plates can be retrieved and transported to a desired surgical site or to the wedge plate tray. In any of the above embodiments, alternatives to the wedge holding forceps described herein can be used to perform the method, provided that the alternative insertion instrument has the elements as described in the various embodiments for the insertion instrument described above.

One advantage of the methods described includes reduced difficulties when placing a mobile wedge plate into an osteotomy with an insertion instrument. Namely, reduced difficulty due to a lack of visualization of the wedge during the placement process. This is because the user is assured that the wedge is well secured and can identify the orientation of the wedge through the alignment of the arms of the insertion instrument. In this way, the user can rotate the bone plate relative to the wedge with confidence when using the insertion instrument as described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant system comprising:
   a bone plate configured to be secured to a bone;
   a wedge adapted to be coupled to the bone plate, the wedge having one of a cavity or a projection;
   an insertion instrument having the other of the cavity or the projection and configured to engage the one of the cavity or the projection of the wedge; and
   a tray adapted to hold the bone plate coupled to the wedge, the tray including an instrument cavity adapted to receive a portion of the insertion instrument and allow the insertion instrument to engage the wedge.

2. The implant system of claim 1, wherein the wedge is moveable with respect to the bone plate.

3. The implant system of claim 1, wherein the insertion instrument further comprises first and second arms pivotally connected to each other, the first arm including one of the cavity or the projection and configured to engage the other one of the cavity or the projection located on the wedge and the second arm including one of a second cavity or a second projection.

4. The implant system of claim 1, wherein the insertion instrument can engage the wedge in a first configuration such that the bone plate is moveable with respect to the insertion instrument and a second configuration such that the bone plate is fixed with respect to the insertion instrument.

5. The implant system of claim 1, further comprising a second cavity or a second projection on the wedge, wherein the one of the cavity or projection is formed on a first surface of the wedge and the second cavity or second projection is formed on a second surface of the wedge opposite the first surface.

6. The implant system of claim 1, wherein the tray further comprises a recessed portion to hold the bone plate, the recessed portion including a first recessed surface and a second recessed surface recessed relative to the first recessed surface, the recessed portion adapted to hold the wedge in place when stored in the tray.

* * * * *